United States Patent [19]
Takeda et al.

[11] Patent Number: 5,474,923
[45] Date of Patent: Dec. 12, 1995

[54] METHOD FOR THE BIOLOGICAL PREPARATION OF HYDROXYVITAMIN D COMPOUNDS

[75] Inventors: Koji Takeda, Fujisawa; Kiyoshi Kimura, Chigasaki; Kazuhiko Okamura; Rokuro Okamoto, both of Fujisawa; Joji Sasaki, Omiya; Takashi Adachi, Saitama; Sadafumi Omura, Ageo, all of Japan

[73] Assignee: Mercian Corporation, Japan

[21] Appl. No.: 711,988

[22] Filed: Jun. 7, 1991

[30] Foreign Application Priority Data

Jun. 15, 1990 [JP] Japan ................................. 2-157054
Nov. 30, 1990 [JP] Japan ................................. 2-334283

[51] Int. Cl.$^6$ ........................................................ C12P 7/02
[52] U.S. Cl. ................................................ 435/127; 435/101
[58] Field of Search ................................... 435/101, 127

[56] References Cited

U.S. PATENT DOCUMENTS 4,892,821  1/1990  Omura et al. ............................. 435/127

FOREIGN PATENT DOCUMENTS

| 298757   | 1/1989  | European Pat. Off. |
| 0298757  | 11/1989 | European Pat. Off. |
| 461921   | 12/1991 | European Pat. Off. |
| 63-41505 | 2/1988  | Japan . |
| 2231089  | 9/1990  | Japan . |
| 8202893  | 2/1982  | WIPO . |

OTHER PUBLICATIONS

Bogoslovskii et al., Proc. Workshop Vitamin D, 7th, 1988 pp. 1021–1023.
Takeda et al., J. Feron, and Bioeng., vol. 78, pp. 380–382, 1994.
Sawada et al, Appl. Microbiol. Biotechnol., 1990, vol. 32, pp. 556–559.

*Primary Examiner*—Irene Marx
*Attorney, Agent, or Firm*—Lorusso & Loud

[57] ABSTRACT

A method for introducing hydroxyl groups into vitamin D compound at the 1α- and/or 25-positions in the presence of a cyclodextrin compound by the use of a reaction mixture containing a microorganism being capable of hydroxylating vitamin D compound or a enzyme produced from the microorganism, is disclosed.

13 Claims, No Drawings

METHOD FOR THE BIOLOGICAL PREPARATION OF HYDROXYVITAMIN D COMPOUNDS

BACKGROUND OF THE INVENTION

1. Field of the Invention

The present invention relates to a method for the biological preparation of 25-hydroxyvitamin D compounds and 1α,25-dihydroxyvitamin D compounds from vitamin D compounds.

2. Prior Art

Vitamin D compounds are known to be important vitamins which participate with absorption of calcium in the body and acceleration of calcium metabolism of the bone, and to be activated by hydroxylating at the 25-position in the liver and at the 1α-position in the kidney [H. F. DeLuca and H. K. Johns, in Ann. Rev. Biochem., vol. 52, page 411 (1983)]. However, patients with liver function disorders are deficient in production content of 25-hydroxyvitamin $D_3$ in the body. Accordingly, administration of 25-hydroxyvitamin $D_3$ to these patients is effective from the viewpoint of a supply of the vitamin deficiency in the body. Furthermore, 1α,25-dihydroxyvitamin $D_3$ has especially strong activity, and shows remarkable effect on patients with renal failure from the same viewpoint as described above. It is known that 1α,25-dihydroxyvitamin $D_3$ can be obtained from 25-hydroxyvitamin $D_3$ as a material by biological and enzymatic chemical conversions (Japanese Patent Kokai 2-469 and ibid. 2-231089). Accordingly, it is industrially advantageous to prepare 25-hydroxyvitamin $D_3$ and 1α,25-dihydroxyvitamin $D_3$ inexpensively.

Direct introduction of hydroxyl groups into vitamin $D_3$ compounds at the 1α- and/or 25-positions by organic synthesis is not known. Such an introduction by using animal organs is known [Biochem. Biophys. Res. Commun., vol. 36, page 251 (1969)], but, this method is not industrially practical. Hydroxylation of vitamin $D_3$ at the 1α- and/or 25-positions by enzymatic chemistry using microorganisms was recently disclosed (Japanese Patent Kokai 2-469 and ibid. 2-231089).

According to the preparations of 25-hydroxyvitamin D compounds and 1α,25-dihydroxyvitamin D compounds by enzymatic chemistry using the microorganisms disclosed in Japanese Patent Kokai 2-469 and ibid. 2-231089, the ratio of conversion from the substrate vitamin $D_3$ and 25-hydroxyvitamin $D_3$ into 25-hydroxyvitamin $D_3$ and 1α,25-dihydroxyvitamin $D_3$, respectively, is not satisfactory. Furthermore, these methods have problems to solve for the industrial preparation, for example, since the concentration of the substrate used is low, these methods need large scale equipment for industrial production.

Thus, an object of the present invention is to provide an improved method for the biological preparation of 25-hydroxyvitamin D compounds and 1α,25-dihydroxyvitamin D compounds from vitamin D compounds and 25-hydroxyvitamin D compounds, respectively, using the prior art microorganisms or enzymes with remarkably increased conversion ratio.

As a result of earnest research in order to increase the ratio of conversion from vitamin D compounds and 25-hydroxyvitamin D compounds into 25-hydroxyvitamin D compounds and 1α,25-dihydroxyvitamin D compounds, respectively, by using microorganisms, the present inventors have found that the conversion ratio is remarkably increased by adding cyclodextrin compounds to a reaction mixture.

SUMMARY OF THE INVENTION

An object of the present invention is to provide a method for the biological preparation of a 25-hydroxyvitamin D compound which comprises adding a vitamin D compound having a hydrogen atom at the 25-position and a cyclodextrin compound to a reaction mixture containing a microorganism being capable of hydroxylating the vitamin D compound or a reaction mixture containing an enzyme produced from the microorganism, and converting the hydrogen atom at the 25-position into a hydroxyl group.

Another object of the present invention is to provide a method for the biological preparation of a 1α,25-dihydroxyvitamin D compound which comprises adding a vitamin D compound having hydrogen atoms at the 1α- and 25-positions and a cyclodextrin compound to a reaction mixture containing a microorganism being capable of hydroxylating the vitamin D compound or a reaction mixture containing an enzyme produced from the microorganism, and converting the hydrogen atoms at the 1α- and 25-positions into hydroxyl groups.

Still other objects of the present invention will become apparent from the following description.

DETAILED DESCRIPTION OF THE INVENTION

The microorganism being capable of hydroxylating vitamin D compounds used in the present invention are Actinomycetales such as, for example, *Nocardia autotrophica* N-102 (FERM BP-1573), *Streptomyces roseosporus* A-5797 (FERM BP-1574), *Streptomyces sclerotialus* T-JSI (FERM BP-1370) and *Amycolata saturnea* FERM BP-2307, all of which are described in Japanese Patent Kokai 2-469 and ibid. 2-231089. Further examples of the microorganisms are Actinomycetales belonging to Amycolata such as *Amycolata saturnea* IFO 14499, *Amycolata autotrophica* ATCC 19727, *Amycolata autotrophica* ATCC 13181, *Amycolata autotrophica* ATCC 33794, *Amycolata autotrophica* ATCC 33795, *Amycolata autotrophica* ATCC 33796, *Amycolata autotrophica* ATCC 33797, *Amycolata autotrophica* JCM 4010 and *Amycolata hydrocarbonoxidans* IFO 14498, all of which are described in Japanese Patent Kokai 2-231089.

Examples of the cyclodextrin compound used in the present invention are α-cyclodextrin, β-cyclodextrin, γ-cyclodextrin, β-dimethylcyclodextrin, β-trimethylcyclodextrin, partially methylated cyclodextrins (e.g. see Japanese Patent Kokai 63-41505; hereinafter referred to as PMCD sometimes) and branched chain cyclodextrins. These cyclodextrin compounds can be used alone or in admixture.

According to the present invention, it is effective to add a detergent together with the cyclodextrin compound. The term detergent as used herein refers to non-ionic detergents such as polyoxyethylene-sorbitan fatty acid ester [e.g. Tween 80 (made by Sigma Co.)], sorbitan fatty acid ester [e.g. Span 85 (made by Sigma Co.)], polyoxyethylene ether [e.g. Brij 96 (made by Sigma Co.) and Triton X-100 (made by Sigma Co.)], nonylphenol [e.g. Nonipol 45 (made by Sanyo Chemical Industries)], and ethylene oxide-propylene oxide brock copolymer [e.g. Pluronic L-62 (made by Asahi Denka Kogyo)]; and anionic detergents such as Dilex (made by Nippon Oil and Fats Co.) and Trax (made by Nippon Oil and Fats Co.).

The Vitamin D compound having hydrogen groups at the 25-position or at the 1α- and 25-positions to be biologically hydroxylated are vitamin $D_2$ derivatives, vitamin $D_3$ derivatives, vitamin $D_4$ derivatives, vitamin $D_5$ derivatives, vitamin $D_6$ derivatives and vitamin $D_7$ derivatives. The hydrogen atom or hydroxyl group at the 17-position side chain of these compounds may be substituted by a halogen atom (e.g. a fluorine atom), a hydroxyl group and a lower alkyl group.

Examples of the substrate compound are vitamin $D_2$, vitamin $D_3$, vitamin $D_4$, vitamin $D_5$, vitamin $D_6$, vitamin $D_7$, 24-oxovitamin $D_3$, 1α-hydroxyvitamin $D_2$, 1α-hydroxyvitamin $D_3$, 1α-hydroxyvitamin $D_4$, 1α-hydroxyvitamin $D_5$, 1α-hydroxyvitamin $D_6$, 1α-hydroxyvitamin $D_7$, 1α-hydroxy-24-oxovitamin $D_3$, 1α,24-dihydroxyvitamin $D_3$, 24-hydroxyvitamin $D_3$, 23-hydroxyvitamin $D_3$, 23-hydroxyvitamin $D_4$, 1α,23-dihydroxyvitamin $D_3$, 1α,23-dihydroxyvitamin $D_4$, 26-hydroxyvitamin $D_2$, 26-hydroxyvitamin $D_3$, 26-hydroxyvitamin $D_4$, 1α,26-dihydroxyvitamin $D_2$, 1α,26-dihydroxyvitamin $D_3$, 1α,26-dihydroxyvitamin $D_4$, 23,24-dihydroxyvitamin $D_3$, 23,26-dihydroxyvitamin $D_3$, 23,26-dihydroxyvitamin $D_4$, vitamin $D_3$-26,23-lactone, 1α-hydroxyvitamin $D_3$-26,23-lactone, 24,24-difluorovitamin $D_3$, 24,24-dichlorovitamin $D_3$, 26,26,26,27,27,27-hexafluorovitamin $D_3$, 24,24-difluoro- 25-hydroxy-26,27-dimethylvitamin $D_3$, 25-hydroxyvitamin $D_2$, 25-hydroxyvitamin $D_3$, 25-hydroxyvitamin $D_4$, 25-hydroxyvitamin $D_5$, 25-hydroxyvitamin $D_6$, 25-hydroxyvitamin $D_7$, 24-oxo-25-hydroxyvitamin $D_3$, 24,25-dihydroxyvitamin $D_3$, 23,25-dihydroxyvitamin $D_3$, 23,25-dihydroxyvitamin $D_4$, 25,26-dihydroxyvitamin $D_2$, 25,26-dihydroxyvitamin $D_3$, 25,26-dihydroxyvitamin $D_4$, and 25-hydroxyvitamin $D_3$-26,23-lactone.

In the method of the present invention, the reaction rate and reaction efficiency are increased by adding a cyclodextrin compound in the absence or presence of a detergent to a reaction mixture containing a microorganism or an enzyme produced from the microorganism. A medium for cultivation of the microorganism having the above ability is chiefly a liquid medium, and the carbon sources are glucose, maltose, sucrose, dextrin, starch, arabinose, xylose, glyceride, plant fats and oils, animal fats and oils, and they are used alone or in admixture. The nitrogen sources used are soybean meal, cotton seed meal, gluten meal, casein, peptone, casamino acid, yeast extract, meat extract and corn steep liquor, and they are used alone or in admixture. In addition, if necessary, organic or inorganic salts can be added in order to aid the growth of the strain and to promote the formation of the enzyme being capable of hydroxylating vitamin D compound at the 25- and 1α-positions.

Preferred cultivations are performed in aerobic conditions such as shake culture and aerated stirring culture at 20° to 33° C., preferably 25° to 30° C. After cultivation for 12–96 hours, preferably 24–48 hours, the substrate vitamin D compound and cyclodextrin are added. If desired, a detergent can be added. The amount of the vitamin D compound is 10–1000 μg/ml, preferably 50–500 μg/ml in a medium. The amount of the cyclodextrin compound is 0.1–15% by weight (1– 1000 mol relative to 1 mol of the vitamin D compound), preferably 0.1–2% by weight (5–140 mol relative to 1 mol of vitamin D compound). The cultivation is carried out at pH 5–9, preferably pH 6–8.

The amount of the detergent is 0.01–5% by weight, preferably 0.05–0.5% by weight in a medium.

According to the method of the present invention, the culture medium or the solution containing the culture mycelium or enzyme is preferably shaked or stirred aerobically. The aerobic stirring is carried out for 1 to 130 hours after addition of the substrate vitamin D compound and a cyclodextrin compound, if desired, and further addition of a detergent. In order to obtain the aerobic conditions, the cultivation is effectively carried out under pressure in an oxygen stream.

A cyclodextrin compound and a detergent can be added together with the substrate vitamin D compound, after or before addition of the substrate vitamin D compound to the reaction mixture.

Isolation of the vitamin D compound thus obtained in the method can be carried out by extraction with an organic solvent, column chromatography and the like. For example, after completion of the reaction, the reaction mixture is extracted with methylene chloride and concentrated to dryness. The residue is dissolved in a suitable solvent such as a mixture of 2-propanol and n-hexane, and the solution, after removal of the insolubles by filtration or centrifugation, is applied to high performance liquid chromatography (HPLC) on silica gel column such as Zorbax SIL (made by Du Pont Co., USA), Shimpac ODS (made by Shimadzu Corporation). and the like to isolate a 25-hydroxyvitamin D compound and/or 1α,25-dihydroxyvitamin D compound.

According to the present invention, active vitamin D compound, i.e. 25-hydroxyvitamin D compound and a 1α,25-dihydroxyvitamin D compound can be prepared by using a microorganism mycelium or the enzyme produced from the mycelium in high efficiency.

The present invention is illustrated but not limited by the following examples. All percents in the examples are % by weight unless otherwise indicated.

EXAMPLE 1

A hundred ml of a medium (BG medium) (pH 7.2) containing 1.5% of bacto-soytone (made by Difco Co.), 0.5% of corn steep liquor, 1.5% of glucose, 0.5% of NaCl and 0.2% of $CaCO_3$, in a 500 ml Erlenmyer flask, was sterilized by autoclaving at 120° C. under pressure for 20 minutes, and inoculated with one platinum loop of *Nocardia autotrophica* N-102 (FERM BP-1573), and shake cultivation was carried out at 28° C. at 230 rpm. On the other hand, 25 mg of vitamin $D_3$ was added to 50 ml of 0.01 M phosphate buffer (pH 7.0) containing 0.15% of a partially methylated cyclodextrin (PMCD, made by Mercian Co.) (in amount of 17 mol of PMCD relative to one mol of vitamin D). After enough stirring, the insolubles were removed by filtration, 10 ml of the filtrate was added to said culture solution (cultivation for 48 hours), and cultivation was continued for a further 48 hours. To 1 ml of the culture medium in a ground stopper tube for centrifugal precipitation were added 2 ml of methanol and 1 ml of chloroform, and stirring was continued for 10 minutes. Furthermore, 1 ml of chloroform and 1 ml of distilled water were added, the mixture was stirred and centrifuged at 3,000 rpm for 5 minutes, and the lower layer was separated. To the upper layer was added 1.5 ml of chloroform, and the mixture was again extracted. The chloroform layers were combined, 0.1 ml of ethanol was added, and the mixture was concentrated to dryness under reduced pressure. The residue was dissolved in 200 μl of n-hexane:2-propanol (86:14) and analyzed by HPLC on Zorbax SIL column (4.6 mm×25 cm) with n-hexane: 2-propanol (86:14) as a mobile phase at a flow rate of 1.5 ml/min.

As a result of detection, the absorption at 265 nm showed the formation of 25.7 μg/ml of 25-hydroxyvitamin $D_3$ (the conversion ratio of the material was 51.4%).

EXAMPLE 2

*Nocardia autotrophica* N-102 in the same BG medium (100 ml/500 ml-Erlenmeyer flask) as used in Example 1 was cultured at 28° C. under the aerobic conditions for 48 hours. To the culture medium were added 10 ml of a 5% PMCD (made by Mercian Co.) solution (0.01 M phosphate buffer, pH 7.0) and a solution of 2% vitamin $D_3$ in 1 ml of ethanol (in amount of 7 mol of PMCD relative to 1 mol of vitamin $D_3$). Further cultivation was continued, and the amounts of 25-hydroxyvitamin $D_3$ shown by the detection similar to that of Example 1 were 21.5 µg/ml, 57.6 µg/ml, 79.2 µg/ml, 92.0 µg/ml and 125 µg/ml (62.5% of the conversion ratio from the material) after cultivation for 24, 48, 72, 96 and 120 hours, respectively. On the contrary, following the same procedure as above but without PMCD, the amount of 25-hydroxyvitamin $D_3$ obtained after caltivation for 96 hours was only 1.69 µg/ml (6.8% of the conversion ratio from the material).

EXAMPLE 3

*Nocardia autotrophica* N-102 in the same BG medium (100 ml/500 ml-Erlenmeyer flask) as used in Example 1 was cultured at 28° C. under the aerobic conditions for 48 hours. To the culture solution were added 10 ml of a 5% PMCD (made by Mercian Co.) solution (0.01 M phosphate buffer, pH 7.0) and a solution of 2% vitamin $D_3$ in 1 ml of ethanol (in the amount of 7 mol of PMCD relative to 1 mol of vitamin $D_3$), and cultivation was continued for a further 96 hours. After completion of the cultivation, 200 ml of methylene chloride was added to the flask, and the mixture was extracted. The methylene chloride layer was concentrated to dryness under reduced pressure, and immediately after the residue was dissolved in 3 ml of 2-propanol:n-hexane (1:9) and allowed to stand at −20° C. for 2 hours. The resulting insolubles were removed by centrifugation. The supernatant was concentrated under reduced pressure and applied to HPLC on Zorbax SIL column (4.6 mm×25 cm) with n-hexane-2-propanol (86:14) as a mobile phase at a flow rate of 1.5 ml/min. The peak fraction at 3.8 minutes was collected, and concentrated to dryness at 40° C. or below under reduced pressure with a nitrogen gas replacement to give 25-hydroxyvitamin $D_3$, which was strictly identical to the authentic sample of the commercially available 25-hydroxyvitamin $D_3$ (made by Duphar Co., Holland) in terms of the retention time of HPLC, the UV absorption spectrum and mass spectrum cleavage pattern.

Maximum UV absorption: $\lambda_{max}$=265 nm (ethanol)

Mass spectrum: 400 ($M^+$), 382 ($M^+$—$H_2O$), 271, 253, 136, 118, 59.

EXAMPLE 4

*Nocardia autotrophica* N-102 in the same BG medium (100 ml/500 ml-Erlenmeyer flask) as used in Example 1 was cultured at 28° C. under the aerobic conditions for 48 hours. To the culture medium were added 10 ml of a 5% PMCD (made by Mercian Co.) solution (0.01 M phosphate buffer, pH 7.0) and a solution of 2% vitamin $D_2$ in 1 ml of ethanol (in the amount of 7 mol of PMCD relative to 1 mol of vitamin $D_2$). Further cultivation was continued, and the amounts of 25-hydroxyvitamin $D_2$ shown by the detection similar to that of Example 1 were 0.5 µg/ml, 55.6 µg/ml, 81.2 µg/ml, 93.0 µg/ml and 128.5 µg/ml (64% of the conversion ratio from the material) after cultivation for 24, 48, 72, 96 and 120 hours, respectively. On the other hand, following a same procedure as described above but without PMCD, the amount of 25-hydroxyvitamin $D_2$ obtained after cultivation for 96 hours was only 1.8 µg/ml (0.9% of the conversion ratio from the material). The retention time of HPLC of 25-hydroxyvitamin $D_2$ was 3.7 minutes.

EXAMPLE 5

*Nocardia autotrophica* N-102 in the same BG medium (100 ml/500 ml-Erlenmeyer flask) as used in Example 1 was cultured at 28° C. under the aerobic conditions for 48 hours. To the culture medium were added 10 ml of a 5% PMCD solution (0.01 M phosphate buffer, pH 7.0) and a solution of 0.1% 1α-hydroxyvitamin $D_3$ in 1 ml of ethanol (in the amount of 140 mol of PMCD relative to 1 mol of 1α-hydroxytvitamin $D_3$). After cultivation for a further 2 hours, methylene chloride was added to the flask, and analysis was carried out according to the method as described in Example 3. The peak fraction having a retention time of 12 minutes was collected, concentrated at 40° C. or below under reduced pressure and applied to HPLC on Zorbax ODS column (4.6 mm×25 cm, made by Du Pont Co., USA) with water-methanol (1:9) as a mobile phase at a flow rate of 1.0 ml/min. After elution, the peak fraction having a retention time of 5.6 minutes was collected and concentrated to dryness at 40° C. or below under reduced pressure with a nitrogen gas replacement to give 650 µg (65% of the conversion ratio from the material) of 1α,25-dihydroxyvitamin $D_3$. On the other hand, following the same procedure as above but without PMCD, the amount of 25-hydroxyvitamin $D_3$ obtained was 350 µg/ml (35% of the conversion ratio from the material).

EXAMPLE 6

*Nocardia autotrophica* N-102 in the same BG medium (100 ml/500 ml-Erlenmeyer flask) as used in Example 1 was cultured with shaking at 28° C. under the aerobic conditions for 72 hours. The culture medium was centrifuged, and the mycelium was collected and washed once with 0.01M tris-acetate buffer (pH 7.4) (containing 2 mM magnesium acetate, 7 mM 2-mercapto ethanol and 20% glycerin), and suspended in 100 ml of the same buffer. The suspension was broken by ultrasonic disintegration (20 kHz, 50 W, for 2 minutes), and centrifuged (10,000 × g, for 15 minutes) to give the supernatant. Polyethylene glycol 6000 was added dropwise slowly to the supernatant to a final concentration of 25%, and the resulting solution was then allowed to stand at 4° C. for 10 minutes. Centrifugation gave the crude enzyme precipitate, 1 g (wet weight) of which was then suspended in 10 ml of tris-acetate buffer (pH 7.4) (containing 70 mM nicotine amide, 2 mM magnesium acetate, 100 mM NADP, 5 mM ATP and 6 mM glucose-6-phosphate). To the suspension were added 5 units of glucose-6-phosphate dehydrogenase, a solution of 20 mg/ml of vitamin $D_3$ in 0.1 ml of ethanol and 1 ml of a 5% PMCD solution (in the amount of 7 mol of PMCD relative to 1 mol of vitamin $D_3$), and the enzyme reaction was carried out at 28° C. with stirring for an hour. The same procedure as described above but without PMCD was followed in order to serve as control. After completion of the reaction, 20 ml of methanol and 10 ml of chloroform were added, and the same determination as described in Example 1 showed the formation of 25-hydroxyvitamin $D_3$ in the amounts of 21.0 µg/ml (10.5% of the conversion ratio from the material) and 7.6 µg/ml (3.8% of the conversion ratio from the material) by the procedure with PMCD and the procedure without PMCD, respectively.

EXAMPLE 7

A hundred ml of a medium (BG medium) (pH 7.2) containing 1.5% of bacto-soytone (made by Difco Co.), 0.5% of corn steep liquor, 1.5% of glucose, 0.5% of NaCl and 0.2% of $CaCO_3$, in a 500 ml Erlenmyer flask, was sterilized by autoclaving at 120° C. for 20 minutes, and inoculated with one platinum loop of *Nocardia autotrophica* N-102 (FERM BP-1573), and shake cultivation was carried out at 28° C. at 230 rpm. After cultivation for 48 hours, 10 ml of a 5% aqueous β-cyclodextrin solution and a solution of 20% Tween 80 in ethanol containing 2% of vitamin $D_3$ were added, and then cultivation was continued for a further 48 hours. To 1 ml of the culture medium, in a ground stopper tube, were added 2 ml of methanol and 1 ml of chloroform, and the mixture was stirred for 10 minutes. Then, 1 ml of chloroform and 1 ml of distilled water were added, and the mixture was stirred and centrifuged at 3,000 rpm for 5 minutes. After removal of the lower phase, the upper phase was extracted with 1.5 ml of chloroform. The chloroform layers were combined, and 0.1 ml of ethanol was added. The mixture was concentrated to dryness under reduced pressure, and the residue was dissolved in 200 μl of n-hexane:2-propanol (86:14), and analyzed by HPLC on Zorbax SIL column (4.6 mm×25 cm) using n-hexane: 2-propanol (86:14) as a mobile phase at a flow rate of 1.5 ml/min.

As a result of detection, the absorption at 265 nm showed the formation of 54.8 μg/ml of 25-hydroxyvitamin $D_3$ (about 27% of the conversion ratio from the material).

To 100 ml of the culture medium was added 200 ml of methylene chloride, and the mixture was extracted. The methylene chloride layer was concentrated to dryness under reduced pressure, and immediately after, the residue was dissolved in 3 ml of 2-propanol-n-hexane (1:9). The solution was allowed to stand at −20° C. for 2 hours, and the resulting insolubles were removed by centrifugation. The supernatant was concentrated under reduced pressure, and applied to HPLC on Zorbax SIL column (4.6 mm×25 cm) with n-hexane:2-propanol (86:14) as a mobile phase at a flow rate of 1.5 ml/min. The peak fraction at 3.8 minutes was collected and concentrated to dryness at 40° C. or below under reduced pressure with a nitrogen gas replacement to give 25-hydroxyvitamin $D_3$, which was strictly identical to the authentic sample of the commercially available 25-hydroxyvitamin $D_3$ (made by Duphar Co., Holland) in terms of the retention time of HPLC, ultraviolet absorption spectrum and mass spectrum cleavage pattern.

Maximum UV absorption: $\lambda_{max}$=265 nm (ethanol)

Mass spectrum: 400 ($M^+$), 382 ($M^+$—$H_2O$), 271, 253, 136, 118, 59.

EXAMPLE 8

In a similar manner to that of Example 1, *Nocardia autotrophica* N-102 (FERM BP-1573) was cultured for 48 hours by using the same BG medium as used in Example 1, and 10 ml of a 5% aqueous α-cyclodextrin solution and a solution of 20% Tween 80 in 1 ml of ethanol containing 2% vitamin $D_3$ were added. The mixture was cultured for a further 48 hours. One ml of the culture medium in a ground stopper tube was determined according to the same method as used in Example 1 to show the formation of 51.5 μg/ml (25.8% of the conversion ratio from the material) of 25-hydroxyvitamin $D_3$.

EXAMPLE 9

Following a conversion from vitamin $D_3$ into 25-hydroxyvitamin $D_3$ in a medium containing 0.2% by weight of Tween 80 using β-dimethylcyclodextrin (made by Toshin Chemical Co.), β-trimethylcyclodextrin (made by Toshin Chemical Co.), a branched chain β-cyclodextrin (made by Nikken Chemical Co.), partially methylated cyclodextrin (made by Mercian Co.) and γ-cyclodextrin (made by Wako Chemical Co.), respectively, in place of β-cyclodextrin in Example 1, there were obtained the results as described in Table 1.

TABLE 1

| Cyclodextrin compound (addition amount: %) | 25-Hydroxyvitamin D after cultivation for 48 hours μg/ml (conversion ratio: %) |
|---|---|
| β-dimethylcyclodextrin (0.5) | 51.0 (25.5) |
| β-trimethylcyclodextrin (1.5) | 47.2 (23.6) |
| branched chain β-cyclodextrin (0.5) | 50.5 (25.3) |
| partially methylated cyclodextrin (0.15) | 47.2 (23.6) |
| γ-cyclodextrin (0.5) | 48.5 (24.2) |
| Control | 7.5 (3.8) |

EXAMPLE 10

Following a conversion from vitamin $D_3$ into 25-hydroxyvitamin $D_3$ similar to that of Example 7 but using Pluronic L-62 (made by Asahi Denka Co.) in place of Tween 80, there was obtained 51.5 μg/ml (25.8% of the conversion ratio) of 25-hydroxyvitamin $D_3$.

EXAMPLE 11

Following a conversion from vitamin $D_3$ into 25-hydroxyvitamin $D_3$ similar to that of Example 7 but using Dilex (made by Nippon Oil and Fats Co. ) in place of Tween 80, there was obtained 42.5 μg/ml (21.2% of the conversion ratio from the material) of 25-hydroxyvitamin $D_3$.

EXAMPLE 12

*Nocardia autotrophica* N-102 in the same BG medium (100 ml/500 ml-Erlenmeyer flask) as used in Example 1 was cultured at 28° C. under the aerobic conditions for 48 hours. To the culture solution were added 10 ml of 5% aqueous β-cyclodextrin solution and a solution of 20% Tween 80 in 1 ml of ethanol containing 2% vitamin $D_3$, and cultivation was continued for a further 48 hours. After completion of the cultivation, following extract and analysis procedures similar to those of Example 1, there was obtained 55.8 μg/ml (27.9% of the conversion ratio) of 25-hydroxyvitamin $D_2$. Following the same procedure without β-cyclodextrin and Tween 80, there was obtained 1.8 μg/ml (0.9% of the conversion ratio from the material) of 25-hydroxyvitamin $D_2$. The retention time of 25-hydroxyvitamin $D_2$ was 3.7 minutes.

EXAMPLE 13

*Nocardia autotrophica* N-102 in the same BG medium (100 ml/500 ml-Erlenmeyer flask) as used in Example 1 was cultured at 28° C. under the aerobic conditions for 48 hours. To the culture medium were added 10 ml of a 5% aqueous β-cyclodextrin solution (0.01 M phosphate buffer, pH 7.0), a solution of 1% 1-hydroxyvitamin $D_3$ in 1 ml of ethanol (in the amount of 140 mol of β-cyclodextrin relative to 1 mol of 1α-hydroxyvitamin $D_3$) and a solution of 20% Tween 80 in 1 ml of ethanol. After cultivation for a further 2 hours, methylene chloride was added to the flask, and the determination as described in Example 1 was carried out. The peak fraction having a retention time of 3.8 minutes was collected, concentrated to dryness at 40° C. or below under reduced pressure, and applied to HPLC on Zorbax ODS (made by Du Pont Co.) with water-methanol (1:9) as a mobile phase at a flow rate of 1.0 ml/min. After elution, the peak reaction having a retention time of 5.6 minutes was collected, and concentrated to dryness under pressure at 40° C. or below with a nitrogen gas replacement to give 645 µg (64.5% of conversion ratio from the material) of 1α,25-dihydroxyvitamin $D_3$. In case of the same procedure as described above but without β-cyclodextrin, the yield was 350 µg (35% of the conversion ratio from the material).

EXAMPLE 14

*Nocardia autotrophica* N-102 in the same BG medium (100 ml/500 ml-Erlenmeyer flask) as used in Example 1 was cultured with shaking at 28° C. under the aerobic conditions for 72 hours. The culture medium was centrifuged, and the mycelia were collected and washed once with 0.01 M tris-acetate buffer (pH 7.4) (containing 2 mM magnesium acetate, 7 mM 2-mercapto ethanol and 20% glycerin), and suspended in 100 ml of the same buffer. The mycelia were disrupted by ultrasonic disintegration (20 kHz, 50 W, for 2 minutes), and centrifuged (10,000 × for 15 minutes) to give the supernatant. Polyethylene glycol 6000 was added dropwise slowly to the supernatant to a final concentration of 25%, and the resulting solution was then allowed to stand at 4° C. for 10 minutes. Centrifugation gave the crude enzyme precipitate, 1 g (wet weight) of which was then suspended in 10 ml of tris-acetate buffer (pH 7.0) (containing 70 mM nicotine amide, 2 mM magnesium acetate, 100 mM NADP, 5 mM ATP and 6 mM glucose-6-phosphoric acid). To the suspension were added 5 units of glucose-6-phosphate dehydrogenase, a solution of 20 mg/ml of vitamin $D_3$ in 0.1 ml of ethanol, 1 ml of a 5% PMCD (made by Mercian Co.) solution (in the amount of 7 mol of PMCD relative to 1 mol of vitamin $D_3$) and a solution of 20% Tween 80 in 1 ml of ethanol, and the enzyme reaction was carried out at 28° C. with stirring for an hour. The same procedure as described above but without a 5% cyclodextrin solution was followed in order to serve as control. After completion of the reaction, 20 ml of methanol and 10 ml of chloroform were added, and the same determination as described in Example 1 showed the formation of 25-hydroxyvitamin $D_3$ in the amounts of 21.0 µg/ml (10.5% of the conversion ratio from the material) and 7.6 µg/ml (3.8% of the conversion ratio from the material) by the procedure with PMCD and the procedure without PMCD, respectively.

EXAMPLE 15

*Nocardia autotrophica* N-102 (FERM BP-1573) in the same BG medium (100 ml/500 ml-Erlenmeyer flask) as used in Example 1 was grown, and 1 ml of which was incubated in 25 ml of TM-1 medium (containing 2% glucose, 0.2% yeast extract, 0.5% peptone (Kyokuto Pharmaceutical Industries Co.), 0.5% corn steep liquor (powder), 1.0% defatted soybean meal, 0.04% $K_2HPO_4$ and 0.4% NaCl, pH 7.0) in a 250 ml Erlenmeyer flask, and cultured at 28° C. for 48 hours. A solution of 2% vitamin $D_3$ in 0.25 ml of ethanol, a detergent Pluronic L-62 and 0.5–1.0 ml of a cyclodextrin compound were added into the flask, and shake cultivation was carried out for a further 90 hours. The formation of 1α,25-dihydroxyvitamin $D_3$ in the culture medium was analyzed according to the same method as described in Example 5, and results were shown in Table 2.

TABLE 2

| Cyclodextrin compound (addition amount: %) | | 1α,25-Dihydroxy-vitamin $D_3$ accumulation (µg/ml) |
|---|---|---|
| α-cyclodextrin | (0.1) | 5.6 |
|  | (0.2) | 6.2 |
| β-cyclodextrin | (0.1) | 15.8 |
|  | (0.2) | 15.4 |
| γ-cyclodextrin | (0.1) | 8.8 |
|  | (0.2) | 12.7 |
| β-dimethylcyclodextrin | (0.1) | 13.0 |
|  | (0.2) | 14.5 |
| β-trimethylcyclodextrin | (0.1) | 5.4 |
|  | (0.2) | 5.0 |
| β-partially methylated cyclodextrin | (0.1) | 6.6 |
|  | (0.2) | 8.4 |
| α-methylated cyclodextrin | (0.1) | 3.0 |
|  | (0.2) | 3.1 |
| Without addition |  | 2.9 |

EXAMPLE 16

*Amycolata autotrophica* ATCC 19727, ATCC 13181, ATCC 33794, ATCC 33795, ATCC 33796, ATCC 33797, JCM 4010, *Amycolata hydrocarbonoxidans* IFO 14498, *Amycolata saturnea* FERM BP-2307 and IFO 14499 were each cultured at 28° C. for 48 hours in the same TM-1 medium as used in Example 15 (50 ml/500 ml-Erlenmeyer flask). A solution of 2% vitamin $D_3$ in 0.5 ml of ethanol, 0.1 g of a detergent Pluronic L-62 and 1.0 ml of 5% β-cyclodextrin were added to the flask, and shake cultivation was carried out for 72 hours. The formation of 25-hydroxyvitamin $D_3$ and 1α,25-dihydroxyvitamin $D_3$ in the culture medium were analyzed according to the same methods as described in Examples 1 and 5, and results were shown in Table 3. Results of control group (without cyclodextrin) were shown in Table 4.

TABLE 3

| | Group with cyclodextrin compound | |
|---|---|---|
| Strain | 25-Hydroxyvitamin $D_3$ (µg/ml) | 1α,25-Dihydroxy-vitamin $D_3$ accumulation (µg/ml) |
| ATCC 19727 | 36.1 | 2.39 |
| ATCC 13181 | 43.6 | 5.84 |
| ATCC 39794 | 45.9 | 4.75 |
| ATCC 39795 | 31.8 | 0.45 |
| ATCC 39796 | 38.9 | 5.02 |
| ATCC 39797 | 36.7 | 7.70 |
| JCM 4010 | 30.9 | 1.41 |
| IFO 14498 | 18.6 | 0.44 |
| IFO 14499 | 36.4 | 1.56 |
| FERM BP-2307 | 37.0 | 1.60 |

TABLE 4

| | Group without cyclodextrin compound | |
|---|---|---|
| Strain | 25-Hydroxyvitamin $D_3$ (µg/ml) | 1α,25-Dihydroxy-vitamin $D_3$ accumulation (µg/ml) |
| ATCC 19727 | 5.0 | 0.04 |
| ATCC 13181 | 2.0 | 0.19 |
| ATCC 39794 | 3.0 | 0.17 |
| ATCC 39795 | 8.0 | 0.01 |
| ATCC 39796 | 9.0 | 0.01 |
| ATCC 39797 | 4.0 | 0.01 |

TABLE 4-continued

| | Group without cyclodextrin compound | |
|---|---|---|
| Strain | 25-Hydroxyvitamin $D_3$ (μg/ml) | $1\alpha,25$-Dihydroxyvitamin $D_3$ accumulation (μg/ml) |
| JCM 4010 | 2.0 | 0.04 |
| IFO 14498 | <1.0 | <0.01 |
| IFO 14499 | 10.0 | <0.01 |
| FERM BP-2307 | 14.0 | <0.01 |

EXAMPLE 17

*Amycolata autotrophica* ATCC 33797 in the same TM-1 medium as used in Example 15 (50 ml/500 ml-Erlenmeyer flask) was cultured at 28° C. for 48 hours. A solution of 2% vitamin $D_3$ in 0.5 ml of ethanol, a detergent Pluronic L-62 and 1.0 ml–2.0 ml of 5% a cyclodextrin compound (or a mixture of different cyclodextrin compounds) were each added into the flask, and shake cultivation was carried out for a further 96 hours. The formation of 25-hydroxyvitamin $D_3$ and $1\alpha,25$-dihydroxyvitamin $D_3$ in the culture medium was analyzed according to the method described in Examples 1 and 5, and results were shown in Table 5.

TABLE 5

| Cyclodextrin compound | 25-Hydroxyvitamin $D_3$ (μg/ml) | $1\alpha,25$-Dihydroxyvitamin $D_3$ (μg/ml) |
|---|---|---|
| β-CD | 28.0 | 7.46 |
| γ-CD | 19.9 | 0.98 |
| β-DCD | 60.8 | 2.72 |
| β-CD + γ-CD | 32.6 | 8.65 |
| β-CD + β-DCD | 74.7 | 3.95 |

β-CD: β-Cyclodextrin (addition amount: 0.2%)
γ-CD: γ-Cyclodextrin (addition amount: 0.2%)
β-DCD: β-Dimethylcyclodextrin (addition amount: 0.2%)?
β-CD + γ-CD: A mixture of β-cyclodextrin and γ-cyclodextrin (each addition amount: 0.2%)
β-CD + β-DCD: A mixture of β-cyclodextrin and β-dimethylcyclodextrin (each addition amount: 0.2%)

What is claimed is:

1. A method for the biological preparation of a 25-hydroxyvitamin D compound which comprises:
   adding a vitamin D compound, having a hydrogen atom at the 25-position, and one or more cyclodextrin compound, to a reaction mixture containing a microorganism or an enzyme extract thereof which is capable of hydroxylating the vitamin D compound, and recovering the 25-hydroxyvitamin D product.

2. A method according to claim 1, wherein a mixture of a solution of the cyclodextrin compound and the vitamin D compound as a substrate is added to the reaction mixture containing a microorganism being capable of hydroxylating the vitamin D compound or reaction mixture containing an enzyme produced from the microorganism.

3. A method according to claim 1, wherein a mixture of different cyclodextrin compounds is added to the reaction mixture.

4. A method according to claim 1, wherein a detergent is added to the reaction mixture.

5. A method according to claim 1, wherein the amount of the cyclodextrin compound added to the reaction mixture is 1 to 1000 mol relative to 1 mol of the vitamin D compound having a hydrogen atom at the 25-position.

6. A method according to claim 1, wherein the 25-hydroxyvitamin D compound is 25-hydroxyvitamin $D_3$, and the vitamin D compound is vitamin $D_3$.

7. A method according to claim 1, wherein the 25-hydroxyvitamin D compound is 25-hydroxyvitamin $D_2$, and the vitamin D compound is vitamin $D_2$.

8. A method for the biological preparation of a $1\alpha,25$-hydroxyvitamin D compound which comprises:
   adding a vitamin D compound, having hydrogen atoms at the $1\alpha$- and 25-positions, and one or more cyclodextrin compounds to a reaction mixture containing a microorganism or an enzyme extract thereof which is capable of hydroxylating the vitamin D compound, and recovering the $1\alpha,25$-dihydroxyvitamin D product.

9. A method according to claim 8, wherein a mixture of a solution of the cyclodextrin compound and the vitamin D compound as a substrate is added to the reaction mixture containing a microorganism being capable of hydroxylating the vitamin D compound or the reaction mixture containing an enzyme produced from the microorganism.

10. A method according to claim 8, wherein a mixture of different cyclodextrin compounds is added to the reaction mixture.

11. A method according to claim 8, wherein a detergent is added to the reaction mixture.

12. A method according to claim 8, wherein the amount of the cyclodextrin compound added to the reaction mixture is 1 to 1000 mol relative to 1 mol of the vitamin D compound having hydrogen atoms at the $1\alpha$- and 25-positions 13. A method according to claim 8, wherein the $1\alpha,25$-dihydroxyvitamin D compound is $1\alpha,25$-hydroxyvitamin $D_3$, and the vitamin D compound is vitamin $D_3$.

* * * * *